United States Patent [19]

Chakrabarti et al.

[11] Patent Number: 5,660,823
[45] Date of Patent: Aug. 26, 1997

[54] FAST DRYING, FILM FORMING IODINE RELEASE SOLUTION

[75] Inventors: Sibu Chakrabarti, Randolph; Anil Menon, West Caldwell, both of N.J.

[73] Assignee: ISP Investments Inc., Wilmington, Del.

[21] Appl. No.: 662,408

[22] Filed: Jun. 12, 1996

Related U.S. Application Data

[63] Continuation-in-part of Ser. No. 541,003, Oct. 11, 1995, abandoned.

[51] Int. Cl.$^6$ .......................... A61K 47/32; A61K 33/18
[52] U.S. Cl. ........................ 424/78.25; 424/78.06
[58] Field of Search ................ 514/772.2; 424/78.25, 424/78.06

[56] References Cited

U.S. PATENT DOCUMENTS

| | | | |
|---|---|---|---|
| 3,216,983 | 11/1965 | Shelanski et al. | 525/60 |
| 3,330,885 | 7/1967 | Dalton et al. | 424/78.25 |
| 4,310,509 | 1/1982 | Berglund et al. | 424/448 |
| 4,323,557 | 4/1982 | Rosso et al. | 424/78.25 |
| 4,584,192 | 4/1986 | Dell et al. | 424/78.25 |
| 5,391,668 | 2/1995 | Tseng et al. | 526/264 |

*Primary Examiner*—Peter F. Kulkosky
*Attorney, Agent, or Firm*—Marilyn J. Maue; Walter Katz; Joshua J. Ward

[57] ABSTRACT

This invention relates to a fast drying iodine complex solution having film forming capability and skin substantivity which solution consists essentially of:

(a) between 1 and 25 wt % polyvinyl pyrrolidone/iodine (PVP/I) complex;

(b) between 5 and 15 wt % vinyl pyrrolidone/vinyl acetate copolymer (PVP/VA);

(c) between 0.5 and 1.5 wt % non-plasticizing polyethylene glycol (PEG);

(d) between 35 and 75 wt % $C_1$ to $C_4$ alkanol;

(e) between 12 and 35 wt % deionized water and (f) between 0 and 2.5 wt % of 1-vinyl-3-(E)-ethylidene pyrrolidone, based on total composition.

The invention also relates to the method of preparing the film forming solution which has a drying time of less than 5 minutes.

7 Claims, No Drawings

5,660,823

FAST DRYING, FILM FORMING IODINE RELEASE SOLUTION

CROSS-REFERENCE TO RELATED APPLICATIONS

This application is a continuation-in-part of application Ser. No. 08/541,003, filed Oct. 11, 1995, now abandoned.

BACKGROUND OF THE INVENTION

Ointments and salves containing an iodine complex are well known and are often applied to gauze and other substrates as wound dressings. However, these vehicles are not altogether satisfactory since the ointment are not film forming and, when dried over an extended time, cake to a crumbly mass. Also, iodine release from the ointment is so slow that higher concentrations of the antimicrobial agent are required or the use of antimicrobial activity boosters are needed to provide efficacious protection against pathogenic micro-organisms and/or infections. Additionally, since ointments are substantially oily they tend to smear and spread over areas surrounding the initial site of application, thereby leading to inefficient use of the medication and possible soiling and staining of clothing. Conversely, solutions of water-like viscosity are also undesirable since their run off rate prevents proper film formation on the skin and transfer of iodine from the carrier to the skin surface. Since a great many microorganisms can survive an initial application of the antimicrobial agent, several reapplications may be necessary in such cases to arrive at a desired result.

The main objective of this invention is to provide a fast drying liquid, antimicrobial formulation which overcomes the above disadvantages.

A further object is to provide a skin substantive solution for effective release of iodine in antimicrobial amounts.

Another object is to provide a commercially feasible and economical method for the preparation of the present film forming medicament.

These and other objects will become apparent from the following description and disclosure.

THE INVENTION

In accordance with this invention, there is provided a fast drying, skin substantive, antimicrobial iodine complex solution having film forming properties which consists essentially of:
 (a) between 1 and 25 wt % polyvinyl pyrrolidone/iodine PVP/I) complex;
 (b) between 5 and 15 wt % vinyl pyrrolidone/vinyl acetate copolymer (PVP/VA);
 (c) between 0.5 and 1.5 wt % non-plasticizing polyethylene glycol (PEG);
 (d) between 35 and 75 wt % $C_1$ to $C_4$ alkanol;
 (e) between 12 and 35 wt % deionized water and
 (f) between 0 and 2.5 wt % of 1-vinyl-3-(E)-ethylidene pyrrolidone, based on total composition.

The VP/VA copolymer in the formulation can comprise 20 to 80% vinyl pyrrolidone (VP) and 80 to 20% VA; about 30% VP and about 70% VA being preferred.

The PEG component is a non-plasticizing compound having 4 to 16 ethylene oxide units and is preferably employed in a concentration of from about 7 to about 12 wt %. The preferred amount of PEG based on PVP/VA copolymer is between about 5 and about 15 wt %.

The alkanol, preferably ethanol, concentration in the composition is most desirably between about 50 and about 70 wt %. Further, the concentration of total water and alkanol in the system is at least 45 wt %, which lower limit is critical since, at about 40 wt %, the mixture displays poor film forming properties and insufficient skin transfer of the antimicrobial agent, iodine. In this regard, the amount of aqueous alkanol solution employed is such that a final product, having a Brookfield viscosity of between about 20 and about 200 cps, preferably between about 20 and about 70 cps, is produced. Similarly the concentration of the total amount of VP in the formulation, including the VP portions in both the copolymer and in the complex, is critical and should not be greater than 25 wt % since above that concentration, the desirable drying time of less than 5 minutes, more often less than 1 minute, is significantly increased and the resulting film begins to show objectionable tackiness in place of the smooth fast drying coatings containing active disinfecting amounts of iodine which characterize the compositions of this invention.

The amount of PVP/I complex component employed herein is that which provides an antimicrobial amount of free iodine for a given purpose or situation and is usually in an amount of between about 9 and about 13 wt % free iodine. The PVP polymer which is complexed with the iodine has a K value between about 12 and about 120 and is commercially available as PLASDONE® and KOLLIDON®.

An additional benefit is realized by the addition of up to 2 wt % 1-vinyl-3-(E)-ethylidene pyrrolidone. As little as from about 0.05 wt % of this compound permits significantly higher loading of the PVP/I component in the formulation, e.g. at least 15% or more, while retaining solution characteristics of the composition.

The present compositions form quick drying films which have a high skin substantivity and a shelf life stability up to at least 6 months. The compositions are non-staining and adhere to the application site without noticeable spreading. These compositions can be applied to the skin in cosmetic or in pharmaceutical formulations wherein the PVP/I is the sole antimicrobial agent or they can be employed in conjunction with other active agents conventionally used in standard cosmetic or pharmaceutical mixtures. These compositions are useful as anticlogging sprays or as liquids which can be dabbed on the skin with an applicator or which can be applied to the skin by any other conventional method of liquid application.

The present compositions are prepared by forming an aqueous solution of PVP/VA copolymer before adding PEG which is dissolved therein. The PVP/I component is then gradually added over a period of from about 15 and about 60 minutes with agitation to effect dissolution before the alkanol is blended into the composition for an additional 5 to 15 minutes. The preparation is carried out at or about ambient temperature and pressure to provide a uniform, clear mixture which is collected as the product of the process.

Having thus described the invention, reference is now had to the following examples which illustrate preferred embodiments or comparative values but which are not to be construed as limiting to the scope of the invention as more broadly set forth above and in the appended claims.

EXAMPLE 1

The following compositions were prepared at room temperature under continuous agitation with a mechanical stirrer over a period of 1.5 hours by introducing PEG into a PVP/VA copolymer aqueous solution followed by PVP/I addition and finally blending in ethanol. The amounts of these components are reported in following Table I along with the Brookfield viscosities (cps) of the products obtained.

TABLE I

| COMPOSITION Ingredients | A QUANTITY | % | B QUANTITY | % | C QUANTITY | % |
|---|---|---|---|---|---|---|
| PVP/I (g) | 100 | 10 | 100 | 10 | 100 | 10 |
| PVP/VA S-630 (g) | 50 | 5 | 100 | 10 | 150 | 15 |
| PEG (g) | 5 | 0.5 | 10 | 1 | 15 | 1.5 |
| Ethanol (ml) | 680 | 67.5 | 560 | 55 | 450 | 43.5 |
| Purified H₂O (ml) | 170 | 17 | 240 | 24 | 300 | 30 |
| PRODUCT | | | | | | |
| Brookfield Visc. (cps) | 20 | | 40 | | 60 | |
| Removable | H₂O wash | | H₂O wash | | H₂O wash | |

The above products are water washable and are removed without staining the skin or clothing in contrast to PVP/I+acrylate polymers which require organic solvents for their removal and which stain the area contacted.

EXAMPLE 2

Each of the above compositions were stored in tightly closed glass bottles at 25°±3° C. for the periods reported below in TABLE II. The % of available (free) iodine was measured initially and at 1 month and 3 month intervals. The results reported in TABLE II show a long shelf life stability of the present formulations.

TABLE II

| COMPOSITION | Initial $I_2$ (%) | After 1 month | After 3 months |
|---|---|---|---|
| A | 13.15 | 12.93 | 12.54 |
| B | 12.80 | 12.00 | 11.84 |
| C | 12.13 | 12.39 | 12.12 |

EXAMPLE 3

Water Leab Solution

When the ratio of PVP/VA to solvent (water) is 1.25:1 a coating of this liquid on the skin failed to dry and remained tacky over the period observed (1 hour). Further, iodine transfer to the skin surface was so slow that twice the amount of the bactericide is needed for an effective antimicrobial dosage.

EXAMPLE 4

Super Dulute Solution

The preparation of composition C was repeated except that 750 ml of water was employed in the formulation. The resulting product ran off the skin when applied, leaving no time for iodine skin transfer at the application site.

EXAMPLE 5

Composition C was repeated using PVP instead of PVP/VA. The film formed was tacky. Surface properties of the film exhibited cracking.

EXAMPLE 6

Composition C was repeated using 1-vinyl-3(E)-ethylidene pyrrolidone (Tseng et al. 5,391,668) at 0.5 and 1%. The viscosity of the solution increased to 85–100 cps. Due to the increased solution viscosity, a larger amount of solution could be applied without affecting film properties. The applied film retained similar characteristics to Composition C corresponding to drying time, and film flexibility. This polymer, at low concentrations, enhances the applied loading capacity of the total solution onto a substrate.

At concentrations of 3 and 4 wt % 1-vinyl-3(E)-ethylidene pyrrolidone concentration, the resulting solution viscosity presents problems in pourability and disposition towards gelling on standing.

What is claimed is:

1. A fast drying, sprayable liquid solution having film forming capability and skin substantivity which solution consists essentially of:

(a) between 1 and 25 wt % polyvinyl pyrrolidone/iodine (PVP/I) complex;

(b) between 5 and 15 wt % vinyl pyrrolidone/vinyl acetate copolymer (PVP/VA);

(c) between 0.5 and 1.5 wt % non-plasticizing polyethylene glycol (PEG);

(d) between 35 and 75 wt % $C_1$ to $C_4$ alkanol;

(e) between 12 and 35 wt % deionized water and (f) between 0 and 2.0 wt % 1-vinyl-3-(E)-ethylidene pyrrolidone, based on total composition.

2. The solution of claim 1 which contains 10 wt % of component (a) and between 5 and 15 wt % of component (c) based on PVP/VA copolymer.

3. The solution of claim 1 or 2 which contains 0.05–1 wt % of component (f).

4. The solution of claim 1 wherein the total amount of VP moiety in the composition is not greater than 25 wt %.

5. The solution of claim 1 wherein the amount of free iodine in the composition is between about 9 and about 13 wt %.

6. The solution of claim 1 wherein the concentration of total water and alkanol is at least 45 wt % of the composition.

7. The process which comprises applying to the skin an antimicrobial amount of the solution of one of claims 1–3.

* * * * *